US011434005B1

(12) United States Patent
Matheson et al.

(10) Patent No.: US 11,434,005 B1
(45) Date of Patent: Sep. 6, 2022

(54) INDOOR DRONE FLIGHT AWARENESS SYSTEM (71) Applicant: United Services Automobile Association (USAA), San Antonio, TX (US)

(72) Inventors: Cory Matheson, Celina, TX (US); Anthony Scott Farnsworth, San Antonio, TX (US); Kathleen L. Swain, Kemah, TX (US); Michael J. Allen, San Antonio, TX (US); Benjamin Ethington, Savannah, TX (US); Jordan A. Newmark, Fair Oaks Ranch, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

(21) Appl. No.: 16/913,854

(22) Filed: Jun. 26, 2020

Related U.S. Application Data (60) Division of application No. 15/927,606, filed on Mar. 21, 2018, now Pat. No. 10,732,626, which is a
(Continued)

(51) Int. Cl.
*H04W 4/024* (2018.01)
*B64C 39/02* (2006.01)
*G06F 3/14* (2006.01)
(Continued)

(52) U.S. Cl.
CPC ....... *B64C 39/024* (2013.01); *G01N 33/0004* (2013.01); *G05D 1/0044* (2013.01); *G05D 1/0094* (2013.01); *G05D 1/02* (2013.01);
*G06F 3/14* (2013.01); *G06Q 40/08* (2013.01); *G06Q 50/163* (2013.01); *G06T 11/206* (2013.01); *G06T 11/40* (2013.01); *G09G 5/12* (2013.01); *G09G 5/37* (2013.01); *H04W 4/02* (2013.01); *H04W 4/024* (2018.02);
(Continued)

(58) Field of Classification Search
CPC ... G06T 11/206; G08C 21/00; G08C 2200/00; G08C 2201/06; G08C 2201/60; G05D 1/0044; H04N 21/42202; H04W 4/02
See application file for complete search history.

(56) References Cited

U.S. PATENT DOCUMENTS 8,098,156 B2 * 1/2012 Caler ................. G08B 25/008
340/541
8,229,768 B1 7/2012 Hopkins, III
(Continued)

OTHER PUBLICATIONS

Chun W.H., Papanikolopoulos N. (2016) Robot Surveillance and Security. In: Siciliano B., Khatib O. (eds) Springer Handbook of Robotics. Springer Handbooks. Springer, Cham, https://doi.org/10.1007/978-3-319-32552-1_61 (Year: 2016).*

*Primary Examiner* — Antonio A Caschera
(74) *Attorney, Agent, or Firm* — BakerHostetler (57) ABSTRACT

Unmanned vehicles can be terrestrial, aerial, nautical, or multi-mode. Unmanned vehicles may be used to survey a property in response to or in anticipation of a security threat or damage to the property. For example, an unmanned vehicle may analyze information about the property and based on the information provide graphics and information associated with the surveying of the property.

20 Claims, 4 Drawing Sheets

Related U.S. Application Data continuation of application No. 15/130,632, filed on Apr. 15, 2016, now Pat. No. 9,939,810.

(60) Provisional application No. 62/148,823, filed on Apr. 17, 2015.

(51) Int. Cl.

| | | |
|---|---|---|
| *G06T 11/40* | (2006.01) | |
| *G06Q 40/08* | (2012.01) | |
| *G06Q 50/16* | (2012.01) | |
| *G01N 33/00* | (2006.01) | |
| *G05D 1/00* | (2006.01) | |
| *G09G 5/37* | (2006.01) | |
| *G05D 1/02* | (2020.01) | |
| *G09G 5/12* | (2006.01) | |
| *H04W 4/02* | (2018.01) | |
| *G06T 11/20* | (2006.01) | |

(52) U.S. Cl.
CPC .... *B64C 2201/12* (2013.01); *B64C 2201/122* (2013.01); *B64C 2201/123* (2013.01); *B64C 2201/127* (2013.01); *B64C 2201/128* (2013.01); *G09G 2370/022* (2013.01)

(56) References Cited

U.S. PATENT DOCUMENTS

| | | |
|---|---|---|
| 9,164,506 B1 | 10/2015 | Zang |
| 9,684,834 B1 | 6/2017 | Ludwig et al. |
| 9,805,582 B2 | 10/2017 | Jedwab |
| 10,134,092 B1 | 11/2018 | Harvey et al. |
| 2002/0012675 A1 | 1/2002 | Jain et al. |
| 2002/0126751 A1 | 9/2002 | Scheurich et al. |
| 2008/0159591 A1 | 7/2008 | Ruedin |
| 2008/0300924 A1 | 12/2008 | Savage et al. |
| 2009/0265193 A1 | 10/2009 | Collins et al. |
| 2010/0004802 A1 | 1/2010 | Bodin et al. |
| 2010/0026489 A1 | 2/2010 | Jordan et al. |
| 2012/0012068 A1 | 1/2012 | Costello |
| 2012/0120268 A1 | 5/2012 | Bockus et al. |
| 2014/0132409 A1 | 5/2014 | Billman et al. |
| 2014/0162583 A1 | 6/2014 | Daly et al. |
| 2014/0267627 A1 | 9/2014 | Freeman et al. |
| 2015/0019267 A1 | 1/2015 | Prieto et al. |
| 2016/0021344 A1* | 1/2016 | Renkis ............... G05D 1/104 901/1 |
| 2016/0282468 A1 | 9/2016 | Gruver et al. |

* cited by examiner

INDOOR DRONE FLIGHT AWARENESS SYSTEM

RELATED APPLICATIONS

This application is a division of Ser. No. 15/927,606 filed on Mar. 21, 2018, which is a continuation of U.S. patent application Ser. No. 15/130,632 filed on Apr. 15, 2016 and issued on Apr. 10, 2018 as U.S. Pat. No. 9,939,810, which claims the benefit of U.S. Provisional Patent Application No. 62/148,823, entitled "Systems and Methods for Indoor Vehicle Utilization," filed Apr. 17, 2015.

BACKGROUND OF THE INVENTION

Unmanned vehicles (e.g., unmanned aerial vehicles) are known for their use in combat zones. In combat zones, they are often used to surveille an area, damage a structures, or lethally wound a potential enemy combatant. The use of unmanned vehicles can go far beyond the aforementioned examples, especially outside of a combat zone and in a commercial setting. Businesses of all sorts are now developing innovative ways to use unmanned vehicles to benefit their business.

SUMMARY

Unmanned vehicles can be terrestrial, aerial, nautical, or multi-mode. Unmanned vehicles may be used to survey inside of a home or other property, map the home, and send data back to a server. Exemplary methods and systems provide feedback about information gathered about a structure. This feedback may help explain the progress of a mission of an unmanned vehicle when traveling around the home. For example, the feedback may be a map that is continually updated on a mobile device synched with the unmanned vehicle.

In one example, a device may include a processor and a memory. The memory may be coupled with the processor and store instructions that when executed the processor cause the processor to effectuate operations such as analyzing information regarding a location, wherein the information comprises sensor information gathered by the at least one sensor of an at least one unmanned vehicle and based on the analyzed information (e.g., number or type of personal items or damage to items), providing instructions to the one or more to a secondary device to display a graphic indicative of a condition of the location (e.g., floor plan or heat map).

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not constrained to limitations that solve any or all disadvantages noted in any part of this disclosure.

BRIEF DESCRIPTION OF THE DRAWINGS

A more detailed understanding may be had from the following description, given by way of example in conjunction with the accompanying drawings wherein.

DETAILED DESCRIPTION

Unmanned vehicles may be used to survey the inside of a structure. For example, an unmanned vehicle may survey a home and, based on the survey, display a map or other information associated with conditions of the property. This disclosure relates at least in part to identifying how unmanned vehicles may communicate with individuals in proximity (or remotely) to the unmanned vehicle.

Figure 1:
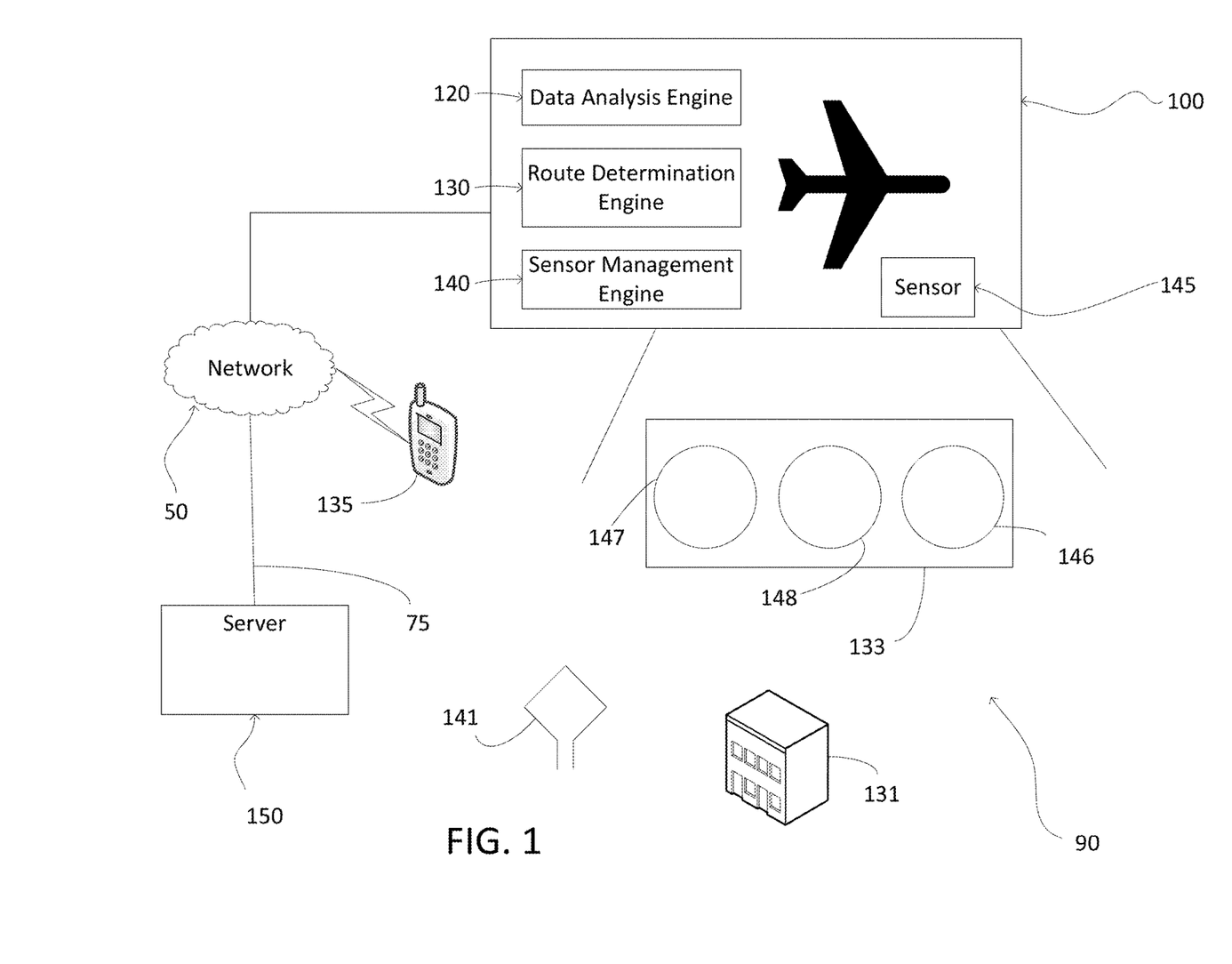
FIG. 1 illustrates an exemplary system associated with unmanned vehicle indoor surveillance of a property.

FIG. 1 illustrates an exemplary system 90 associated with unmanned vehicle surveillance of a property. Unmanned vehicle 100 includes sensor 145, data analysis engine 120, route determination engine 130, and sensor management engine 140. Unmanned vehicle 100 may be communicatively connected with network 50, server 150, and mobile device 135. A business (e.g., an insurance provider) may own or have control of unmanned vehicle 100, network 50, or server 150. Unmanned vehicle 100 may include floor plan 133 of structure 131 (e.g., a commercial building or home) that it may surveille. Floor plan 133 may be based on information such as previous surveillance of inside structure 131, information about structures with similar dimensions as structure 131, information about structures approximate (e.g., 1 mile) to structure 131, or the like. The dimensions of structure 131 may be obtained by using satellite images, government property records, or the like. Floorplan 133 may be divided into multiple areas, such as area 146, area 147, and area 148. In a first example, area 146, area 147, and area 148 may correspond to rooms, such as bedroom, bathroom, or kitchen. In a second example, sectors may also be an indication of expected (or surveilled) concentration of items (e.g., furniture or other belongings) within structure 131.

Figure 4:
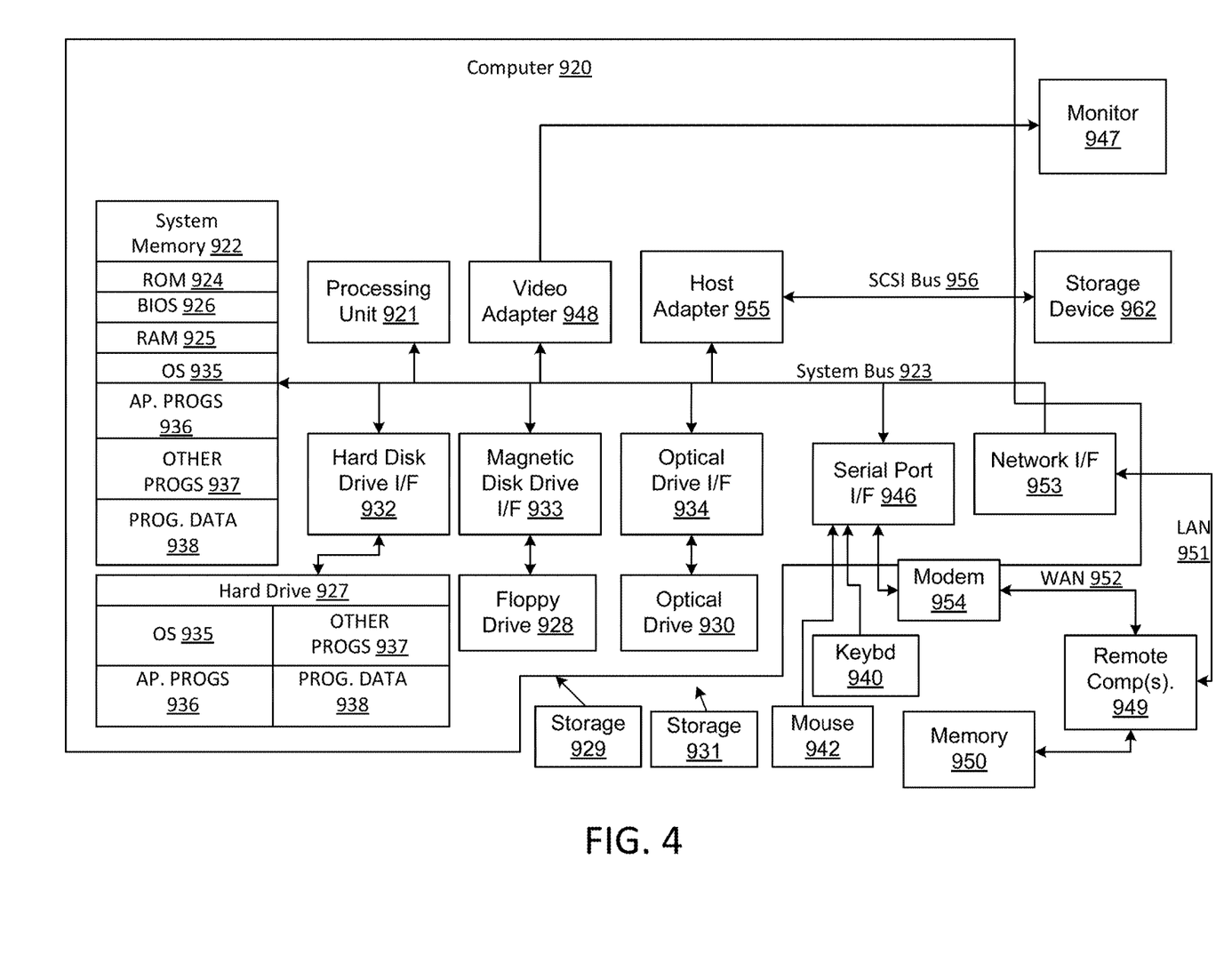
FIG. 4 is an exemplary block diagram representing a computer system in which aspects of the methods and systems disclosed herein or portions thereof may be incorporated.

With continued reference to FIG. 1, data analysis engine 120, route determination engine 130, and sensor management engine 140 are logical entities that may be implemented in the form of software (e.g., computer-executable instructions) stored in a memory of, and executing on a processor of unmanned vehicle 100, server 150, mobile device 135, or another computer system such as illustrated in FIG. 4. Data analysis engine 120 may analyze data retrieved by sensor 145. Analysis by data analysis engine 120 may include comparing image data to stored coordinates to identify additional or replacement images that may need to be gathered. Route determination engine 130 may be utilized to manage unmanned vehicle 100, which may include confirming that unmanned vehicle 100 remains on a planned path based on a particular mission. Route determination engine 130 may also determine modifications to a route of unmanned vehicle 100 based on gathered data. For example, if additional images are needed of a certain location, which may include a different perspective or angle, route determination engine 130 may request unmanned vehicle 100 to vary the planned path accordingly, which may change the parameters of the mission. Unmanned vehicle 100 may communicate with external sensors or data sources (e.g., external sensor 141) that provide information to unmanned vehicle 100 to execute the indoor systems as discussed herein. External sensor 141 may be part of a smart home and provide information that alters the mission of unmanned vehicle 100 (e.g., a higher priority action needs to be executed based on changed environmental conditions). One or more external sensor 141 may be used to assist unmanned vehicle 100 to maneuver indoors.

Sensor management engine 140 controls sensor 145. This control may include determining which sensor of a plurality of sensors are gathering data, the operating characteristics of said data gathering (e.g., the level of zoom of a visible light camera), where sensor 145 is aimed, or any other sensor performance control variables. It is contemplated herein that sensor 145 may include a visible light camera, an infrared camera, a microphone, a particle inspection device (e.g., a device that can detect what compounds are in sampled air gathered by unmanned vehicle 100), radar emitting/detecting device(s), a spectrometer, a hyperspectral sensor, a temperature sensor, a humidity sensor, a gas sensor, or a navigation sensor, among other things.

Figure 2:
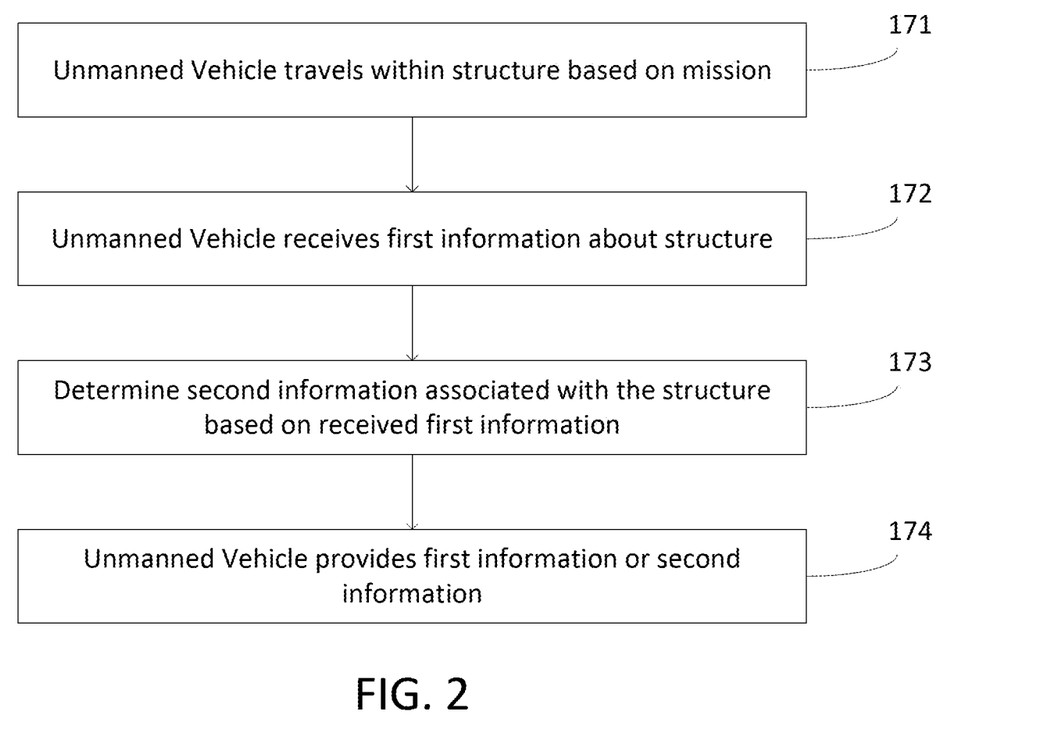
FIG. 2 illustrates an exemplary method for processing surveillance data associated with an unmanned vehicle.

FIG. 2 illustrates an exemplary method or processing surveillance data associated with an unmanned vehicle. At step 171, unmanned vehicle 100 travels within structure 131 based on a mission. The mission may be associated with a notification that structure 131 has been damaged (e.g., structure 131 owner contacted his/her insurance company), a notification of a hazard in structure 131, or the mission may be a periodic deployment to gather additional information about structure 131, among other things. The gathering of additional information may be used to provide suggestions for ways to secure property, to update an assessment of value of property, observe violations of use of structure 131 (e.g., unauthorized pets), or the like. Unmanned vehicle 100 may use floor plan 133 of structure 131 to help navigate traveling through structure 131.

Nearly concurrent with mission generation, route determination engine 130 may receive a map (e.g. floor plan 133) that wholly or partially details the location where unmanned vehicle 100 has been tasked to survey. The map may be a basic overview of where structural elements are (e.g., where walls, windows, stairs, and doors are located), or it may be a detailed description of where individual items (e.g., couch, lamp) are located, including what condition said items are in. This mission may be generated and executed before an incident occurs (e.g., for the purposes of identifying dispositions and/or conditions of one or more objects that maybe covered by an insurance policy). During execution of the mission (step 171), unmanned vehicle 100 is deployed in and around structure 131 (e.g., a residence). Unmanned vehicle 100 may be operated remotely via a person, natively via software executed on unmanned vehicle 100, remotely via software executed at least in part on server 150, or combinations thereof. As unmanned vehicle 100 navigates inside structure 131, navigational rules may be utilized by unmanned vehicle 100 to inform or dictate operation of unmanned vehicle 100. For example, unmanned vehicle 100 may enter a room and/or a room may become visible to vehicle (e.g., unmanned vehicle 100 is in a doorway to the room).

It is contemplated that as unmanned vehicle 100 travels throughout structure 131 it may travel into areas that may be considered sensitive to occupants of structure 131. There is a potential that at times it may be inappropriate for unmanned vehicle 100 to travel into or take a picture of a bedroom, bathroom, or other area. Systems may be put into place in order to reduce undesired entry into an area or use of sensors by unmanned vehicle 100, while staying on mission for inventorying a house, for example. In a first scenario, there may be a method for deactivating sensor 145 of unmanned vehicle 100 based on the presence or absence of a user within proximity (e.g., 6 to 8 feet). The user may be identified by facial recognition, presence of a mobile device, or the like. In a second scenario, unmanned vehicle 100 may enter certain areas after conducting a "virtual knock" or having a positive response to a "virtual knock." A virtual knock may be considered any sending of a message associated with text (e.g., a question), graphics, sound (e.g., sound of a knock), voice (e.g., voice request to enter), vibration (e.g., vibration pattern), or the like in order to alert of eminent access to or to gain access to an area, or to activate sensor 145 of unmanned vehicle 100. In an example, after sensing mobile device 135 in area 147, unmanned vehicle 100 may send a message to mobile device 135 that cause three vibrations (knock, knock, knock). Unmanned vehicle 100 may enter area 147 after receiving an appropriate response (e.g., text message, voice command, gesture, body movement, or the like), if required. Unmanned vehicle 100 may send a broadcast message that is not directed to any particular sensed device or user that covers area 147. In another example, unmanned vehicle 100 may only turn on a particular sensor after receiving an appropriate response from a virtual knock within area 147. Any combination of location of a user, location of unmanned vehicle 100 in the home, time of day, period, or the like are contemplated for the methods of deactivating sensor 145 or attempting a virtual knock. If unmanned vehicle 100 is not authorized to go into an area, it may surveille authorized areas and then perform another virtual knock when it is ready to return to the previously not authorized area.

At step 172, unmanned vehicle 100 may receive first information about structure 131. In an example, unmanned vehicle 100 may use any number of sensors 145 to obtain first information such as, location or height of doorways, presence of people or animals, type of furniture, number of personal items, or the like data. This data gathering (step 172), and associated analysis (step 173), may assist unmanned vehicle 100 in identifying objects within the room (e.g., lamp, television, couch, window), and the orientation of the objects (e.g., the lamp is upright or on its side). These determinations may optionally be compared to data that indicates a previous state of the room (e.g., data that may have been previously gathered by unmanned vehicle 100 before an insurance claim-generating event transpired). The determinations may also be used to supplement or update one or more maps. The analysis may further be utilized to determine if additional information is needed. For example, if an object is determined to be on its side, the identification of such a condition may indicate the need for further imagery of that object with particular focus on whether any damage has been sustained by the object as it was moved. Alternatively or in combination therewith, unmanned vehicle 100 may receive additional commands that alter or add to the mission of unmanned vehicle 100. First information (e.g., raw data or analyzed data) may be sent back to server 150 or processed on unmanned vehicle 100.

In another example, information may be gathered from other devices (e.g., building cameras or motion detectors), approximate to unmanned vehicle 100. It is contemplated herein that structure 131 may include any type of electronic-based system that is involved with managing/monitoring/controlling a property. For example, structure 131 may monitor what appliances are being operated, monitor what the conditions are (movement in a room, temperature of each room), or actually controls aspects of structure 131 (e.g., if no one is home, reset the thermostat to a temperature that is less expensive to maintain).

With continued reference to FIG. 2, at step 173, there may be a determination of second information associated with structure 131 based on the first information received at step 172. The second information may be text, graphics, or vibrations, among other things that may alert mobile device 135 or a user. The analysis of first information may include cost analysis of the objects in structure 131. For example, if a couch is damaged or destroyed, the analysis may include a determination of the amount of damages that are compensable. This determination of compensable damages, at least in part, may be based on a comparison between presently gathered data and previously gathered data. It is contemplated herein that the previously gathered data may have been gathered by unmanned vehicle 100, mobile device 135, or by other devices.

At step 174, the second information of step 173 or first information of step 172 may be provided in one or more forms to server 150, mobile device 135, or other devices. In an example, unmanned vehicle 100 may be synched to mobile device 135 (e.g., mobile phone or wearable device) and relay second information to mobile device 135. The second information may be text, graphics, or vibrations, among other things that may alert mobile device 135. For example, unmanned vehicle 100 may send a progress bar to mobile device 135 that alerts of general progress of the mission (e.g., mission to inventory items in structure 131 at step 1 of 10). In another example, unmanned vehicle 100 may send a text or video alert to mobile device 135 in order to make a user aware of an issue that should be looked into with regard to structure 131 (e.g., a video of possible roof leak area).

Figure 3:
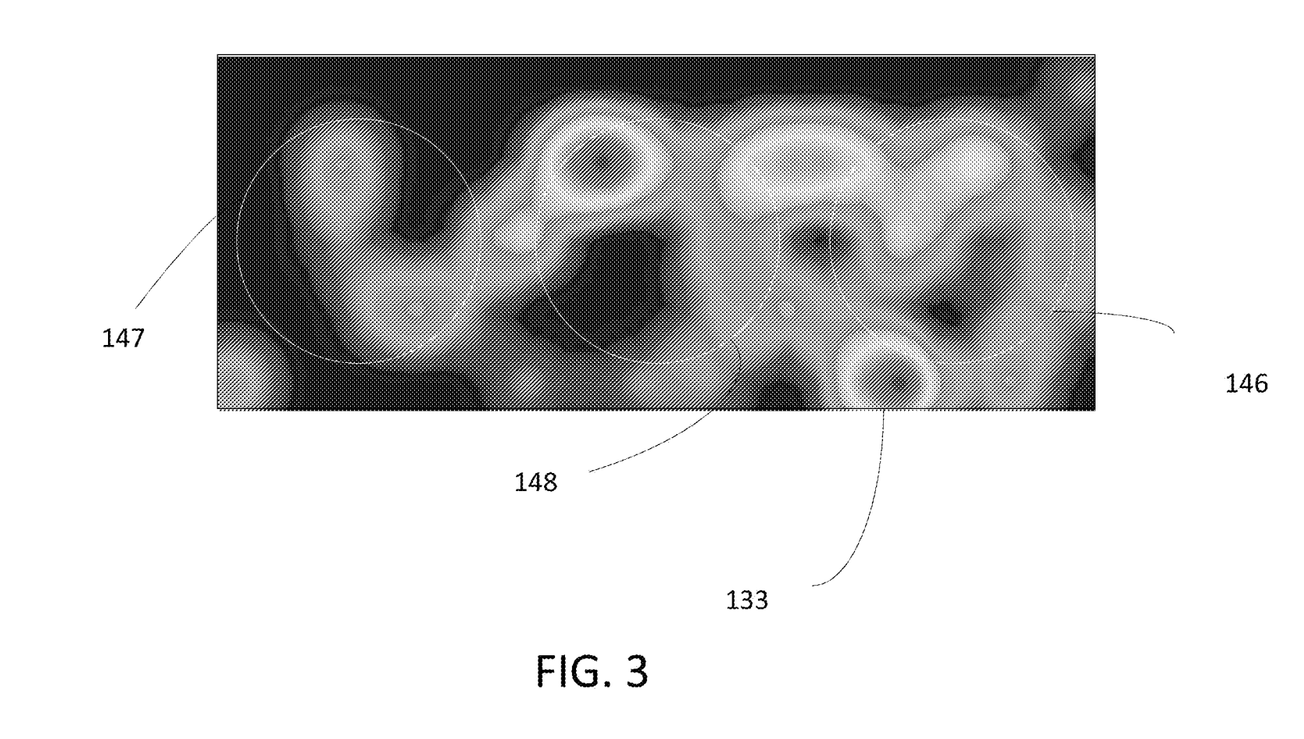
FIG. 3 illustrate an exemplary map of a surveilled area.

Second information 174 may be a heat map in which a graphical representation of data is based on first information and represented as colors. FIG. 3 illustrates an exemplary heat map in the context of floor plan 133 of structure 131. For example, the heat map may be indicative of where there is the most damage or potential for damage to structure 131 or items within structure 131. The heat map may be indicative of where valuables are located in structure 131 or the likely of valuables in an area to be in jeopardy in view of natural disasters or manmade events (e.g., theft or fire). The heat map may show information about problematic utility issues (e.g., water, gas, electricity) or problematic areas for particular natural disasters. The heat map may show areas to avoid in a natural disaster. The heat map may help direct the assessment of an area by insurance agents, public safety officials, or others. This may help expedite an in-person visit inside structure 131. The heat map may also allow for some level of privacy since colors and shapes may be used instead of camera video of actual objects in structure 131. Second information, such as the heat map of FIG. 3, may be used for subsequent surveillance of structure 131 by unmanned vehicle 100. Unmanned vehicle 100 may use a threshold level of color or intensity on heat map to determine navigation, use of sensors, or retrieval of information. Priority or order of navigation of unmanned vehicle may be based on the heat map or other second information. The use of certain sensors 145 may be based on observed intensity of the heat map or other second information. Although heat maps are discussed herein, other second information such as text and digital voice may be used to convey similar information as the heat map.

Discussed below is additional updated information (e.g., feedback) that may be provided from unmanned vehicle 100. The system discussed herein gives a user feedback with regard to what has been done by the unmanned vehicle 100 while surveilling structure 131. The feedback may be a map of the home, a bar chart, a graphical representation of progress or percentage complete of a mission of unmanned vehicle 100, or the like. In addition, unmanned vehicle 100 may take inventory or assess damage and then provide a report that includes listing inventory of structure 131 or listing items that need repair in structure 131, respectively. The feedback provided by unmanned vehicle 100 to mobile device 135, for example, may be done in near real-time. The determination of unmanned vehicle 100 to provide feedback may be based on meeting certain threshold levels. The threshold levels may be based on time, type or level of sensor information received, or the like.

Herein are several different examples associated with unmanned vehicle service delivery. It is contemplated herein that methods, components, or the like of each example may be reasonably integrated with or removed from other examples discussed herein. Additional examples are discussed below.

In a use case, unmanned vehicle 100 may provide services, such as might be useful in a domestic setting. Thus, it is contemplated herein that unmanned vehicle 100 may be programmed to check on people. In one example, unmanned vehicle 100 may be sent to check on children (e.g., based on a specific command or based on a recurring hourly schedule). Unmanned vehicle 100 may sense the child (e.g., baby), send a notification about the child's state (e.g., asleep, awake, crying, has recently cried) and/or the state of an object in the room (e.g., the child's toy is on the floor and the child cannot reach it). In another example, unmanned vehicle 100 may identify an object that a person needs (e.g., a child's toy, person's medicine) and endeavor to bring that item to the person. In yet another example, unmanned vehicle 100 may be tasked with various other household chores, such as retrieving a newspaper, turning off/on a light, retrieving a beverage and checking if a bed is made.

In another use case, unmanned vehicle 100 may be controllable by multiple sources. For example, unmanned vehicle 100 may initially be controlled remotely by a central computer system (e.g., server 150 in FIG. 1). After initial deployment unmanned vehicle 100 may be remotely controlled by a person via sever 150, and then when onsite unmanned vehicle 100 may be controlled by software within unmanned vehicle 100. Further, unmanned vehicle 100 may be controllable by an individual onsite. In one example, unmanned vehicle 100 may be controlled by and follow an insurance adjustor, public safety official, or another user. In another example, unmanned vehicle 100 may be controllable by residents. For instance, a person may take control of unmanned vehicle 100 via a personal computing device (e.g., cell phone, tablet) or via voice commands. And subsequent to a person (e.g., a child) taking control of unmanned vehicle 100, another person (e.g., the child's parent) may take control of unmanned vehicle 100 from the first person. Thus, unmanned vehicle 100 may be programmed to utilize an order of priority in following commands. In yet another example, unmanned vehicle 100 may be tasked to follow around or act in coordination with a person, such as an adjustor. In this example, unmanned vehicle 100 may be provided with interactive capabilities (e.g., voice recognition software to understand and perform commands from the adjustor, software to interact with an application on the adjustor's cell phone). Thus, unmanned vehicle 100 and adjustor may combine to gather the desired information.

In yet another use case, unmanned vehicle 100 may work in coordination with a security system. For example, if an intrusion is detected by a home security system, unmanned vehicle 100 may investigate the event. For instance, if motion is detected in a room, unmanned vehicle 100 may be sent to determine what event is causing the motion. It is contemplated herein that unmanned vehicle 100 and a home's security system may be configured to cooperatively function such that system's 100 movements are ignored by the security system.

While unmanned vehicle 100 is investigating an event/potential intrusion, unmanned vehicle 100 may identify the cause (e.g., a pet moving around), and notify the security system or the manager/owner of the location that the cause of the alarm has been determined to be innocuous. Alternatively, unmanned vehicle 100 may determine that an unauthorized/unknown person is in the location, and as a result may contact the authorities (e.g., the police). It is further contemplated herein that unmanned vehicle 100 may be configurable to close windows/doors so as to enable a security system to be turned on or reset.

Navigational rules for unmanned vehicle 100 may include rules that detail a distance for unmanned vehicle 100 to stay away from people, walls, and/or objects. It is contemplated herein that certain objects (e.g., crystal and/or glass objects) may be associated with a larger buffer distance than other objects (e.g., a couch). In one example, vehicle's navigational rules suggest that unmanned vehicle 100 stay at least four feet above the floor, at least two feet below the ceiling, and to stay at least three feet from objects in the room. As discussed herein, unmanned vehicle 100 may turn off or turn on different sensors 145 or features based on proximity to a person (or mobile device associated with that person). For example, all recording capability of unmanned vehicle 100 may be shutoff within 5 feet of a particular user.

It is further contemplated herein that unmanned vehicle 100 may operate in conjunction and/or cooperation with multiple other unmanned vehicles. In this way, unmanned vehicle 100 may transfer or reallocate missions or sub-missions to other unmanned vehicles for which said missions and/or sub-missions would be easier to perform.

It is further contemplated herein that unmanned vehicle 100 may operate in coordination with one or more other system's 100. For example, first unmanned vehicle 100 may operate with a first person for their tasks (e.g., retrieve beverages), and second unmanned vehicle 100 may operate with a second person for their tasks (e.g., check on the status of other people in a home), and the two systems may combine to create a super unmanned vehicle 100 with the functionality that combines the functionality of first unmanned vehicle 100 and second unmanned vehicle 100.

In another embodiment, unmanned vehicle 100 may provide cell phone and/or satellite phone uplink and/or unmanned vehicle 100 could operate as a repeater to the same (and as such multiple unmanned vehicles 100 may be daisy chained together to provide communication abilities). Another network feature that may be included is that vehicle 100 may provide network connectivity, such as cell phone tower (e.g., by imitating a cell phone tower) and/or a Wi-Fi network.

It is to be appreciated that network 50 depicted in FIG. 1, for example, may include a local area network (LAN), a wide area network (WAN), a personal area network (PAN), or combinations thereof. Such networking environments are commonplace in offices, enterprise-wide computer networks, intranets, and the Internet. For instance, when used in a LAN networking environment, system 90 is connected to the LAN through a network interface or adapter (not shown). When used in a WAN networking environment, the computing system environment typically includes a modem or other means for establishing communications over the WAN, such as the Internet. The modem, which may be internal or external, may be connected to a system bus via a user input interface, or via another appropriate mechanism. In a networked environment, program modules depicted relative to system 90, or portions thereof, may be stored in a remote memory storage device such as storage medium. Computing devices may communicate over network 50 through one or more communications links 75 formed between data interfaces. Communication links 75 may comprise either wired or wireless links. It is to be appreciated that the illustrated network connections in the figures (e.g., FIG. 1 or FIG. 4) are exemplary and other ways of establishing a communications link between multiple devices may be used.

FIG. 4 and the following discussion are intended to provide a brief general description of a suitable computing environment in which the methods and systems disclosed herein or portions thereof may be implemented. Although not required, the methods and systems disclosed herein is described in the general context of computer-executable instructions, such as program modules, being executed by a computer, such as a client workstation, server, personal computer, or mobile computing device such as a smartphone. Generally, program modules include routines, programs, objects, components, data structures and the like that perform particular tasks or implement particular abstract data types. Moreover, it should be appreciated the methods and systems disclosed herein and/or portions thereof may be practiced with other computer system configurations, including hand-held devices, multi-processor systems, microprocessor-based or programmable consumer electronics, network PCs, minicomputers, mainframe computers and the like. A processor may be implemented on a single-chip, multiple chips or multiple electrical components with different architectures. The methods and systems disclosed herein may also be practiced in distributed computing environments where tasks are performed by remote processing devices that are linked through a communications network. In a distributed computing environment, program modules may be located in both local and remote memory storage devices.

FIG. 4 is a block diagram representing a general purpose computer system in which aspects of the methods and systems disclosed herein and/or portions thereof may be incorporated. As shown, the exemplary general purpose computing system includes a computer 920 or the like, including a processing unit 921, a system memory 922, and a system bus 923 that couples various system components including the system memory to the processing unit 921. The system bus 923 may be any of several types of bus structures including a memory bus or memory controller, a peripheral bus, and a local bus using any of a variety of bus architectures. The system memory includes read-only memory (ROM) 924 and random access memory (RAM) 925. A basic input/output system 926 (BIOS), containing the basic routines that help to transfer information between elements within the computer 920, such as during start-up, is stored in ROM 924.

The computer 920 may further include a hard disk drive 927 for reading from and writing to a hard disk (not shown), a magnetic disk drive 928 for reading from or writing to a removable magnetic disk 929, and an optical disk drive 930 for reading from or writing to a removable optical disk 931 such as a CD-ROM or other optical media. The hard disk drive 927, magnetic disk drive 928, and optical disk drive 930 are connected to the system bus 923 by a hard disk drive interface 932, a magnetic disk drive interface 933, and an optical drive interface 934, respectively. The drives and their associated computer-readable media provide non-volatile storage of computer readable instructions, data structures, program modules and other data for the computer 920. As described herein, computer-readable media is a tangible, physical, and concrete article of manufacture and thus not a signal per se.

Although the exemplary environment described herein employs a hard disk, a removable magnetic disk 929, and a removable optical disk 931, it should be appreciated that other types of computer readable media which can store data that is accessible by a computer may also be used in the exemplary operating environment. Such other types of media include, but are not limited to, a magnetic cassette, a flash memory card, a digital video or versatile disk, a Bernoulli cartridge, a random access memory (RAM), a read-only memory (ROM), and the like.

A number of program modules may be stored on the hard disk, magnetic disk 929, optical disk 931, ROM 924 or RAM 925, including an operating system 935, one or more application programs 936, other program modules 937 and program data 938. A user may enter commands and information into the computer 920 through input devices such as a keyboard 940 and pointing device 942. Other input devices (not shown) may include a microphone, joystick, game pad, satellite disk, scanner, or the like. These and other input devices are often connected to the processing unit 921 through a serial port interface 946 that is coupled to the system bus, but may be connected by other interfaces, such as a parallel port, game port, or universal serial bus (USB). A monitor 947 or other type of display device is also connected to the system bus 923 via an interface, such as a video adapter 948. In addition to the monitor 947, a computer may include other peripheral output devices (not shown), such as speakers and printers. The exemplary system of FIG. 4 also includes a host adapter 955, a Small Computer System Interface (SCSI) bus 956, and an external storage device 962 connected to the SCSI bus 956.

The computer 920 may operate in a networked environment using logical connections to one or more remote computers, such as a remote computer 949. The remote computer 949 may be a personal computer, a server, a router, a network PC, a peer device or other common network node, and may include many or all of the elements described above relative to the computer 920, although only a memory storage device 950 has been illustrated in FIG. 4. The logical connections depicted in FIG. 4 include a local area network (LAN) 951 and a wide area network (WAN) 952. Such networking environments are commonplace in offices, enterprise-wide computer networks, intranets, and the Internet.

When used in a LAN networking environment, the computer 920 is connected to the LAN 951 through a network interface or adapter 953. When used in a WAN networking environment, the computer 920 may include a modem 954 or other means for establishing communications over the wide area network 952, such as the Internet. The modem 954, which may be internal or external, is connected to the system bus 923 via the serial port interface 946. In a networked environment, program modules depicted relative to the computer 920, or portions thereof, may be stored in the remote memory storage device. It will be appreciated that the network connections shown are exemplary and other means of establishing a communications link between the computers may be used.

Computer 920 may include a variety of computer readable storage media. Computer readable storage media can be any available media that can be accessed by computer 920 and includes both volatile and nonvolatile media, removable and non-removable media. By way of example, and not limitation, computer readable media may comprise computer storage media and communication media. Computer storage media include both volatile and nonvolatile, removable and non-removable media implemented in any method or technology for storage of information such as computer readable instructions, data structures, program modules or other data. Computer storage media include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other medium which can be used to store the desired information and which can be accessed by computer 920. Again, as described herein, computer-readable media is a tangible, physical, and concrete article of manufacture and thus not a signal per se. Combinations of any of the above should also be included within the scope of computer readable media that may be used to store source code for implementing the methods and systems described herein. Any combination of the features or elements disclosed herein may be used in one or more examples.

In describing preferred examples of the subject matter of the present disclosure, as illustrated in the Figures, specific terminology is employed for the sake of clarity. The claimed subject matter, however, is not intended to be limited to the specific terminology so selected, and it is to be understood that each specific element includes all technical equivalents that operate in a similar manner to accomplish a similar purpose.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A unmanned vehicle, the unmanned vehicle comprising:
a processor; and
a memory coupled with the processor, the memory having stored thereon executable instructions that when executed by the processor to cause the processor to effectuate operations comprising:
obtaining, from a security system, instructions to identify the cause of a detected motion within a structure; and
transmitting, to the security system,
instructions to disregard movement of the unmanned vehicle within the structure.

2. The unmanned vehicle of claim 1, the operations further comprising notifying the security system that the cause of the detected motion is innocuous.

3. The unmanned vehicle of claim 1, the operations further comprising notifying the security system that the cause of the detected motion is innocuous, wherein the cause of the detected motion is a pet.

4. The unmanned vehicle of claim 1, the operations further comprising:

obtaining a notification that the cause of the detected motion is unauthorized; and contacting authorities about the cause of the detected motion.

5. The unmanned vehicle of claim 1, the operations further comprising closing a window to enable the security system to be turned on.

6. The unmanned vehicle of claim 1, the operations further comprising closing a door to enable the security system to be turned on.

7. The unmanned vehicle of claim 1, the operations further comprising closing a window to enable the security system to be reset.

8. The unmanned vehicle of claim 1, the operations further comprising closing a door to enable the security system to be reset.

9. The unmanned vehicle of claim 1, the operations further comprising obtaining navigational rules to keep a buffer distance based on a type of object.

10. The unmanned vehicle of claim 1, the operations further comprising obtaining navigational rules to keep a buffer distance based on a type of object, wherein a buffer distance for a fragile object is larger than a buffer distance for a durable object.

11. The unmanned vehicle of claim 1, the operations further comprising obtaining navigational rules to keep a buffer distance based on a type of object, wherein a buffer distance for a glass object is larger than a buffer distance for a durable object.

12. The unmanned vehicle of claim 1, the operations further comprising relaying the instructions to another unmanned vehicle to cooperatively identify the cause of the detected motion within the structure.

13. The unmanned vehicle of claim 1, the operations further comprising relaying the instructions to another unmanned vehicle to identify the cause of the detected motion within the structure instead of the unmanned vehicle.

14. The unmanned vehicle of claim 1, the operations further comprising:

based on a comparison of unmanned vehicle and another unmanned vehicle performance for identifying the cause of the detected motion, relaying the instructions to the another unmanned vehicle to identify the cause of the detected motion within the structure instead of the unmanned vehicle.

15. The unmanned vehicle of claim 1, the operations further comprising:

generating a heat map that is indicative of the condition of the structure, wherein the heat map is:

a graphical representation of data based on gathered information about a structure, and the graphical representation of data is represented as colors; and navigating the unmanned vehicle based on the colors of the heat map.

16. The unmanned vehicle of claim 1, the operations further comprising:

generating a heat map that is indicative of the condition of the structure, wherein the heat map is:

a graphical representation of data based on gathered information about a structure, and the graphical representation of data is represented as colors; and surveilling the structure based on the colors of the heat map.

17. The unmanned vehicle of claim 1, the operations further comprising surveilling the structure based on colors of a heat map associated with valuables within the structure.

18. A method comprising:

obtaining, by a computing device from a security system, instructions to identify the cause of a detected motion within a structure; and transmitting, by the computing device, to the security system, instructions to disregard movement of the unmanned vehicle within the structure.

19. The method of claim 18, wherein the method further comprises notifying, by the computing device, the security system that the cause of the detected motion is innocuous.

20. The method of claim 18, wherein the method further comprises closing, by the computing device, a window or door to enable the security system to be turned on or reset.

* * * * *